United States Patent [19]
Pollack et al.

[11] Patent Number: 5,945,542
[45] Date of Patent: Aug. 31, 1999

[54] ISOLATION OF NATURAL L-β-3-INDOLYLALANINE AND ENRICHMENT OF NATURAL ALIPHATIC AMINO ACID MIXTURES WITH NATURAL L-β-3-INDOLYLALANINE

[75] Inventors: Robert L. Pollack, 8442 Chippewa Rd., Philadelphia, Pa. 19128; John C. Godfrey, 1649 Old Welsh Rd., Huntingdon Valley, Pa. 19006-5835

[73] Assignees: Robert L. Pollack, Philadelphia; John C. Godfrey, Huntingdon Valley, both of Pa.

[21] Appl. No.: 09/030,952

[22] Filed: Feb. 26, 1998

[51] Int. Cl.$^6$ .......................... C07D 209/20; B01D 15/08
[52] U.S. Cl. .......................... 548/497; 548/496; 210/661
[58] Field of Search .......................... 562/443; 548/496, 548/497

[56] References Cited

PUBLICATIONS

"Adsorption Chromatography of Phenylalanine" *Biotechnology and Bioengineering,* A.M. de Hollanda e Vasconcellos et al, 33(Apr.):1324–1329 (1989).

"Adsorption of Phenylalanine from Casein Hydrolysates" *Applied Biochemistry and Biotechnology,* A.M.H. Vasconcellos et al, 37:69–80 (1992).

*Harper's Biochemistry,* 21st Ed. 1988. R.K. Murray, D.K. Granner, P.A. Mayes and V.W. Rodwell. Section V. Biochemistry of Extracellular & Intracellular Communication, pp. 445–462. Appleton & Lange. Norwalk, Connecticut/San Mateo, California.

"Evaluation of L–tryptophan for Treatment of Insomnia: A Review". D. Schneider–Helmert and C.L. Spinweber, *Psychopharmacology* (1986) 89:1–7.

"L–tryptophan: A Rational Hypnotic with Clinical Potential". E. Hartmann. *Am. J. Psychiatry* (1977) 134(4) : 366–370.

"Dietary Effects on Brain Serotonin Synthesis: Relationship to Appetite Regulation". J.D. Fernstrom. *Am.J.Clin.Nutr.* (Nov. 1985) 42:1072–1082.

"Acute Tryptophan Depletion and Increased Food Intake and Irritability n Bulimia Nervosa". T.E. Weltzin, M.H. Fernstrom, J.D. Fernstrom, S.K. Neuberger and W.H. Kaye, *Am.J.of Psychiatry* (1995) 152(11):1668–1671.

"The Effect of Low Brain Serotonin on Mood and Aggression in Humans. Influence of Baseline Mood and Genetic Factors." S.N. Young, R.O. Pihl, C. Benkelfat, R. Palmour, M. Ellenbogen and D. Lemarquand. *Recent Advances in Tryptophan Research.* Ed. G.A. Filippini et al, pp. 45–50, Plenum Press, New York, 1996.

"Tryptophan Depletion and Aggressive Responding in Healthy Males". F.G. Moeller, D.M. Dougherty, A.C. Swann, D. Collins, C.M. Davis and D.R. Cherek. *Psychopharmacology,* (1996) 126:97–103.

"Aggression and Personality: Association with Amino Acids and Monoamine Metabolites". S.E. Moller, E.L. Mortensen, L. Breum, C. Alling, O.G. Larsen, T. Boge–Rasmussen, C. Jensen and K. Bennicke. *Psychological Medicine* (1996) 26:323–331.

"The Effects of Dietary Tryptophan on Chronic Maxillofacial Pain and Experimental Pain Tolerance". S. Seltzer, D. Dewart, R.L. Pollack and E. Jackson. *J. Psychiat. Res.* (1982/1983) 17 (2):181–186.

"Alteration of Human Pain Thresholds by Nutritional Manipulation and L–Tryptophan Supplementation". S. Seltzer, R. Stoch, R. Marcus and E. Jackson. *Pain* (1982) 13:385–393.

"Effects of Altering Brain Serotonin Activity on Human Chronic Pain". In *Advances in Pain Research and Therapy.* J.J. Bonica and Albe–Fissard, Eds. vol. 1, 601–606. Raven Press 1976, New York.

*Primary Examiner*—Gary Geist
*Assistant Examiner*—Brian J. Davis
*Attorney, Agent, or Firm*—Breiner & Breiner

[57] ABSTRACT

A process for isolating substantially pure natural L-β-3-indolylalanine (L-β-3) from a mixture of amino acids, such as a protein hydrolysate, is described. A protein hydrolysate, for example of casein or soy protein, is passed over a polymeric resin attractive to aromatic amino acids but not attractive to aliphatic amino acids. The aromatic amino acids are retained on the resin while the aliphatic amino acids pass over the resin and are collected. The resin is then washed with water to displace any residual aliphatic acids which may be physically associated with but not bound to the resin. Thereafter, the resin is eluted with a dilute acid to displace L-phenylalanine and L-tyrosine and provide a solution thereof while allowing L-β-3 to be retained on the resin. The resin is then further eluted with a dilute base to displace L-β-3 from the resin and provide a solution of L-β-3. Substantially pure natural L-β-3 is recoverable from this solution.

14 Claims, No Drawings

ISOLATION OF NATURAL L-β-3-INDOLYLALANINE AND ENRICHMENT OF NATURAL ALIPHATIC AMINO ACID MIXTURES WITH NATURAL L-β-3-INDOLYLALANINE

FIELD OF INVENTION

The invention relates generally to the isolation of natural L-β-3-indolylalanine (L-β-3) and the provision of natural amino acid mixtures enriched with natural L-β-3. The L-β-3 and amino acid mixtures containing L-β-3 provide dietary therapeutic supplements for increasing the production of serotonin within the brain, thereby decreasing or eliminating undesirable physiological conditions brought about by a decreased brain serotonin level.

BACKGROUND OF THE INVENTION

In order for multicellular organisms to function, it is necessary for the cells of a body to communicate with each other. In this way, it is possible to coordinate responses as required to constantly adjust to a continually changing external and internal environment [1]. This communication process is dependent on two operating systems, i.e., the nervous system in which signals or messages are transmitted, and hormones which are secreted and transported to adjacent or distant tissues. Both of these systems initiate specific physiological actions dependent on the particular type of cell that is activated.

The first step in the transmission of a brain signal is the synthesis of a chemical molecule called a neurotransmitter. Of the many brain neurotransmitters that have been identified, several are not synthesized de novo in nerve terminals, but rather are the result of a series of enzymatic reactions which modify a precursor molecule, usually an amino acid. After the molecules of the neurotransmitter have been biosynthesized, they are stored in the axon terminals of pre-synaptic nerve fibers in tiny membrane-bound sacs called synaptic vesicles which serve to protect the neurotransmitter molecules until they are used.

Serotonin is a neurotransmitter which the brain utilizes to send messages (electrical impulses) from one brain cell to another. Brain levels of serotonin have been shown to be involved in diverse physiologic processes, the most studied being sleep, appetite, mood, and pain threshold. Biochemical disturbances in the brain resulting in reduced levels of serotonin have been linked to insomnia [2][3], excessive appetite and weight gain [4][5], clinical depression, aggressiveness [6][7][8], and lowered pain threshold [9][10][11]. The latter abnormality results in chronic, intractable pain that generally is refractory to treatment by conventional medications.

The neurotransmitter serotonin is synthesized in the brain from the amino acid L-β-3. L-β-3 cannot be made in the body. L-β-3 must be introduced into the body from an outside source, such as from protein in food or as a dietary supplement. Along with the other amino acids present in the blood stream (which are absorbed from the small intestine from hydrolytic digestive processes in the gastrointestinal tract), L-β-3 is carried to the brain. In the brain, a very selective process then takes place prior to the formation of serotonin.

In order for L-β-3 to be converted to serotonin, L-β-3 must first cross a separating mechanism that exists between the blood vessels in the brain and the brain proper. For L-β-3 to pass from the circulating blood through the blood/brain barrier, a transport mechanism in the form of a carrier protein is required. The primary function of this mechanism is to isolate L-β-3 from the majority of other amino acids circulating in the blood and, then, literally to transport L-β-3 across this selective blood/brain barrier into the brain. There, a two-step enzymatic process converts the L-β-3 first to 5-hydroxy-L-β-3 and then to serotonin.

L-β-3, however, is not the only amino acid carried by this transport mechanism. Five other amino acids, termed large neutral amino acids (LNAAs), are carried as well. LNAAs include phenylalanine, tyrosine, leucine, isoleucine, and valine. L-β-3 not only has to compete with these LNAAs for access to the transport mechanisms, but L-β-3 also has a lower affinity for the carrier system than do the LNAAs. Of the five LNAAs, phenylalanine is the most tightly bound to the transport protein and is therefore the most detrimental to the transport of L-β-3 across the blood/brain barrier. To complicate this situation further, L-β-3 in foods is present in lower amounts than the LNAAs, particularly in animal proteins. All of these factors converge to limit the amount of L-β-3 that gets through to the brain to be finally converted into serotonin.

It is known that dietary supplementation with L-β-3 increases the blood level of L-β-3 and facilitates the passage of L-β-3 across the blood/brain barrier into the brain. The increased amount of L-β-3 in the brain permits a greater amount of L-β-3 to be converted to serotonin. There are, however, numerous conditions that can interfere with and decrease the amount of L-β-3 that normally passes through the blood/brain barrier into the brain each day. The primary factor that controls the degree to which L-β-3 is transported across the blood/brain barrier is the ratio of L-β-3 to LNAAs that is present in the blood going to the brain. At a lower-than-normal L-β-3 to LNAA ratio, the number of molecules of L-β-3 present at the blood/brain barrier is less than normal. The LNAAs, which are normally present in larger numbers than L-β-3, then overwhelm the L-β-3 by monopolizing the majority of the transport carriers, and even less L-β-3 passes across the blood/brain barrier and into the brain as compared to the number of LNAAs that are passed across the barrier. In attempting to correct this improper L-β-3/LNAA ratio, it was found that increasing dietary protein intake in order to add more L-β-3 to the system can result, paradoxically, in an even greater derangement of the L-β-3/LNAA ratio because of the simultaneous greater intake of LNAAs over the intake of L-β-3.

One means by which the L-β-3/LNAA ratio abnormality can be treated is by the administration of L-β-3 without the accompanying presence of the LNAAs, especially without the presence of phenylalanine. This administration of L-β-3 serves to increase the L-β-3 portion of the circulating L-β-3/LNAA ratio, increase the amount of L-β-3 which will be transported across the blood/brain barrier into the brain, increase the L-β-3 pool in the brain, and increase the rate of conversion of L-β-3 to serotonin.

Prior to 1989, L-β-3 was available to consumers as a dietary supplement and could be purchased freely. Studies on the oral administration of L-β-3 under proper dietary conditions that provided a supplementary intake of this particular amino acid showed that supplemental L-β-3 helped to correct an improper L-β-3/LNAA ratio in the brain. This increased level of brain L-β-3 directly produced an increased brain serotonin level which was associated with a reduction or elimination of serotonin-deficiency syndromes.

In the late 1980's, none of the L-β-3 available in nationally-marketed preparations was produced in the United States. All of the L-β-3 used in the United States was imported from Japan. In 1989, the importation and sale of L-β-3 in the U.S. was halted by the U.S. Food and Drug Administration (FDA) as a result of a highly toxic contaminant that was found in batches of L-β-3 made by a bacterial fermentation process used by one particular Japanese company. To date, the importation of L-β-3 into the U.S. and the sale of all imported L-β-3-containing products has not resumed. L-β-3 is still unavailable to the public because of the difficulty in excluding possible toxic compounds which could be generated in L-β-3 produced by fermentative processes.

Natural L-β-3 is the only substance which will increase brain serotonin in a normal physiological manner. A need exists for natural L-β-3 which can serve as a direct precursor for the synthesis of serotonin in the brain, serve as a source of serotonin which is free of the many side effects encountered with the use of serotonin-enhancing medications, and is obtained in a manner which ensures that no potentially toxic compounds are produced by the microorganism which produces the L-β-3 as a part of its metabolic cycle.

OBJECTS AND BRIEF DESCRIPTION OF THE INVENTION

The invention relates to L-β-3 as a naturally-occurring amino acid found in all common dietary proteins; as the amino acid naturally used by the body to produce serotonin in the brain; and as obtained simply and directly from natural dietary proteins, thereby being free of biologically produced contaminants.

Thus, primary objects of the invention include separation of the amino acid L-β-3-indolylalanine from a natural source of a mixture of amino acids, preferably enzymatic or other natural protein hydrolysates containing mixtures of free amino acids; preparation of an amino acid fraction from the aforementioned L-β-3 and an amino acid mixture (obtained during the aforementioned separation) that is free of aromatic amino acids, particularly phenylalanine; and preparation of highly enriched mixtures of L-β-3 and one or more non-aromatic amino acids, i.e., mixtures having a concentration of L-β-3 in an amount greater than that which occurs naturally.

More particularly, the invention is directed to providing processes, and compositions based on compounds obtained by such processes, for (1) the separation, as a group, of aromatic amino acids, including L-β-3, from an amino acid mixture, the mixture preferably being obtained by the hydrolysis of common proteins normally used for dietary purposes; (2) the removal of L-β-3 from the mixture of aromatic amino acids obtained in (1); and (3) producing mixtures of one or more non-aromatic amino acids with the recovered L-β-3 in various proportions. All components isolated or recovered in the process of the invention are provided in a form suitable for further use.

The invention provides a process whereby a mixture of natural amino acids containing substantially all of the natural amino acids (i.e., glycine, the L-forms of alanine, arginine, asparagine, aspartic acid, cysteine, glutamic acid, glutamine, histidine, hydroxyproline, L-β-3, isoleucine, leucine, lysine, methionine, phenylalanine, proline, serine, threonine, tyrosine, and valine) in the form of free amino acids is separated into three fractions containing, respectively, (a) substantially all of the non-aromatic amino acids originally present, i.e., alanine, arginine, asparagine, aspartic acid, cysteine (in equilibrium with the dimeric cystine), glutamic acid, glutamine, glycine, histidine, hydroxyproline, isoleucine, leucine, lysine, methionine, proline, serine, threonine, and valine; (b) the monocyclic aromatic amino acids phenylalanine and tyrosine; and (c) L-β-3, the only amino acid of the group that possesses as a part of its structure two fused aromatic rings.

The invention further provides a range of mixtures of fraction (a) with fraction (c) while specifically eliminating fraction (b) which is deleterious to the desirable physiological actions of L-β-3. These mixtures including one or more aliphatic amino acids and L-β-3 are possessed of highly desirable physiological properties useful in the therapeutic relief of human suffering related to and caused, at least in part, by a relative deficiency of L-β-3.

The present invention involves the discovery that when a mixture containing phenylalanine, tyrosine, and L-β-3 in the presence of mixed aliphatic amino acids is dissolved in water and applied or exposed by contact to a porous, wettable polymeric resin having attraction for aromatic rings of amino acids but little or no attraction to aliphatic amino acids at the natural pH of the solution, that the mixed aromatic amino acids adsorb selectively to the resin and can thereafter themselves be selectively and sequentially desorbed. This is accomplished by first taking a natural amino acid-containing mixture or source, preferably an enzymatic or other natural protein hydrolysate, dissolving it in water, and passing it over a polymeric resin having properties as described above, preferably a non-ionic cross-linked polystyrene, in order that the three aromatic amino acids will be selectively attracted to the resin and the aliphatic amino acids carried away in the fluid carrier. The resin is thereafter washed with deionized water to remove any residual non-aromatic or aliphatic amino acids which, while having essentially no affinity for the resin, may be physically associated with but not bound by attractive forces to the resin. Then the resin is subjected to serial elutions with a suitable dilute acid and dilute base. Suitable acids are short chain aliphatic acids having molecular weights no greater than 88.10 daltons and a Ka between from $1.77 \times 10^{-4}$ to $1.34 \times 10^{-5}$ ($pK_a$ of between from 3.75 to 4.87) at 25° C. Suitable bases are ammonia and short chain aliphatic primary secondary or tertiary amines having molecular weights no greater than 101.19 daltons and a $K_b$ between from $1.26 \times 10^{-3}$ to $1.8 \times 10^{-5}$ ($pK_b$ of between from 2.90 to 4.74) at 25° C. A preferred acid and base is dilute acetic acid and dilute ammonium hydroxide, respectively, from the standpoint of both function and economy. The resin is first washed with the dilute acid to selectively desorb phenylalanine and tyrosine from the resin while leaving L-β-3 adsorbed to the resin. The resin is then washed with deionized water to remove the acid. Thereafter, the resin is washed with the dilute base to displace the L-β-3 from the resin. Both the acid and the base will form weak salts with amino acids, which readily decompose upon gentle heating. Since both the acid and the base are very volatile and amino acids are not, the solutions can readily be heated under vacuum to remove water and either the acid (from the phenylalanine plus tyrosine fraction) or the base (from the L-β-3 fraction) leaving behind the free amino acids in substantially pure form. This evaporative concentration when performed on the L-β-3-containing solution provides a dry, non-hygroscopic powder while removing excess base. Alternatively, the L-β-3 is recovered by crystallization. The serial elutions with dilute acid and dilute base allow the L-β-3 first to be held to the polymeric resin while removing phenylalanine and tyrosine and, thereafter, isolating the L-β-3 from a major amount of other amino acids, as well as residual dipeptides, in the starting hydrolysate mixture. It is particularly advantageous to remove phenylalanine from L-β-3 since, as described above, phenylalanine is strongly competitive with L-β-3 in the key systems which transport L-β-3 to the brain.

All of the examples herein are based upon the use of an enzymatic hydrolysate of casein. An enzymatic hydrolysate of soy protein is also useful and is highly preferred since it contains twice as much free L-β-3 as does casein hydrolysate. Other natural protein hydrolysates are necessarily also useful. The particular hydrolysate used will depend on availability. The protein hydrolysate used can be "concentrated" in the sense that a higher amount of protein hydrolysate is present to the amount of water when put in solution as compared to conventional preparations. The protein hydrolysate is generally present in an amount of 1–30% by wt. of the aqueous solution containing the protein hydrolysate. A preferred range for the present invention is 5 to 16% by weight. Most food-acceptable protein sources contain L-β-3 at about 0.5 to 1.5% by weight of the contained protein. The invention serves to concentrate the L-β-3 from these sources to a range of about at least 10 to 75%.

Suitable polymeric resins for use in the invention are porous wettable polymeric resins which have little attraction to aliphatic amino acids but are attractive to aromatic rings of amino acids. The attraction to the aromatic rings of amino acids is believed to be based on the polymeric resin having attractive van der Waals interaction due to the π-electrons of the polymer with the π-electrons of the aromatic rings of the amino acids. A preferred polymeric resin suitable for use in the present invention is a nonionic cross-linked polystyrene such as sold under the name AMBERLITE® XAD-4 resin sold by Rohm & Haas Company. Other polymeric resins also sold by Rohm & Haas which are suitable for use include, but are not limited to, the following: Amberlite XAD-16, Amberlite XAD 1180, Amberlite XAD-2000, Amberlite XAD-2010, Diaion HP20, Diaion HP20SS, Sepabeads SP20MS, Amberchrom CG-71, Amberchrom CG-161, Amberchrom CG-300, Amberchrom CG-1000, Ambersorb 563, Ambersorb 575, Ambersorb 348F, and Ambersorb 572. The resins are preferably present in particulate form, most preferably in the form of porous beads.

Suitable acids, in dilute form, suitable for use include, but are not limited to, acetic acid, formic acid, propionic acid, and butyric or i-butyric acid. As stated above, dilute acetic acid is preferred.

Suitable bases, in dilute form, suitable for use include, but are not limited to, ammonia (in the form of ammonium hydroxide), trimethylamine, triethylamine, $(CH_3)_2NH$, $(C_2H_5)_2NH$, $CH_3NH_2$ and $CH_3CH_2NH_2$. Ammonium hydroxide is preferred.

The invention is further understood and described by the following examples which serve to illustrate, but not limit, the present invention.

EXAMPLE 1

Fractionation Of A Digest Of Casein Which Contains L-β-3

This example describes the general procedure for the preparation of the fractions containing (a) substantially all of the non-aromatic amino acids originally present in the source containing a mixture of natural amino acids, i.e., alanine, arginine, asparagine, aspartic acid, cysteine (in equilibrium with the dimeric cystine), glutamic acid, glutamine, glycine, histidine, hydroxyproline, isoleucine, leucine, lysine, methionine, proline, serine, threonine, and valine; (b) the monocyclic amino acids phenylalanine and tyrosine; and (c) L-β-3.

A glass column, having the dimensions of 1 cm (inner diameter)×30 cm and containing approximately 24 grams of AMBERLITE® XAD-4 (a completely nonionic cross-linked polystyrene adsorbent in the form of white insoluble beads having an average diameter of 0.30 to 0.45 mm), was prepared according to the resin manufacturer's (Rohm and Haas Company) general directions for carrying out the adsorptive separation of aromatic from non-aromatic organic compounds. Briefly, the column was loosely wet-packed by pouring a suspension of the resin beads in water into the top of the column until the top of the settled bead layer was within 1 cm of the top of the column. The column was then arranged to backwash (bottom to top) with water at a rate sufficient to expand the apparent column volume by 50%. Backwash with water was continued for ten minutes. The flow was then stopped and the resin beads were allowed to settle under the influence of gravity only, in order to achieve uniform packing of the column. After passing approximately 25 ml of water in the downward direction, down-wash was continued with 108 ml of 91% (weight/volume, aqueous) isopropyl alcohol in 37.5 minutes. The alcohol wash was followed by a wash with 432 ml of water during 1.25 hours, at an approximate flow rate of 9.6 ml/min. The resin column thus prepared was ready for the adsorptive separation of the mixed, free amino acids.

The starting material for the adsorptive separation of the mixed free amino acids had the following characteristics: a refined, enzymatic hydrolysate of casein as a dry powder containing 80% free amino acids, the remainder being almost entirely residual dipeptides. In terms of amino acid composition, the hydrolysate contained 819.5 mg/g of non-aromatic amino acids, 40.9 mg/g of L-phenylalanine plus L-tyrosine, and 5.7 mg/g of L-β-3.

A clear solution of the above starting material was prepared from 7.800 g of the hydrolysate in 78 ml of water at room temperature. This solution was applied to the resin column in five portions over 20 minutes at a flow rate of 4.0 ml/min. Elution with plain water was continued until 341 ml of eluate was collected in 3 yellow fractions of 104 ml, 124 ml, and 113 ml. Evaporation to dryness of these first 3 fractions yielded, respectively, 6.578 g, 1.016 g, and 0.107 g. Thin layer chromatography (TLC) demonstrated that these 3 fractions contained only the non-aromatic amino acids, i.e., they contained no L-phenylalanine, L-tyrosine, or L-β-3. Elution was then continued with 150 ml of 2% acetic acid in water, followed by 150 ml of water, and four fractions totaling 287 ml were collected. On evaporation to dryness, the fractions contained, respectively, 70.1 mg, 27.2 mg, 22.6 mg, and 13.2 mg of substance which was shown by TLC to consist of L-phenylalanine, L-tyrosine, and a trace amount of L-β-3. Elution was then continued with 100 ml of 1.0 N ammonium hydroxide, followed by 75 ml of water. Two fractions, totaling 178 ml, were collected. On evaporation to dryness, these fractions yielded a total of 70.6 mg of substance. TLC revealed that only L-β-3 was present. Since the recovery of L-β-3 was substantially greater than that expected from the reported content of 5.7 mg/g in the starting material, it is clear that the reported, estimated contents of amino acids in the starting material is an approximation. Nevertheless, the total weight recovered in all fractions from this column, 7.805 g, was very close to the input of 7.800 g.

EXAMPLE 2

Scale-up Of Fractionation Of An Enzymatic Digest Of Casein

Employing a column of the same dimensions and prepared in the same manner with AMBERLITE® XAD-4 resin beads as in Example 1, 10.000 g of the same casein enzymatic hydrolysate was dissolved in 78 ml of water and applied to the column during 21 minutes, followed by elution with water at a flow rate of 3.6 ml/min. Fractions were collected as follows:

| Fraction No. | Color | Volume (ml) |
| --- | --- | --- |
| 1 | yellow | 133.2 |
| 2 | pale yellow | 99.0 |
| 3 | faint yellow | 101.9 |

The eluant was changed to 2% acetic acid in water, 155 ml, followed by elution with water, and the following fractions were collected, all at a flow rate of 3.6 ml/min.:

| Fraction No. | Color | Volume (ml) |
| --- | --- | --- |
| 4 | none | 78.5 |
| 5 | none | 91.4 |
| 6 | none | 81.6 |
| 7 | none | 59.4 |

The eluant was changed to 100 ml of 1 N ammonium hydroxide, followed by elution with water at a flow rate of 4.0 to 4.2 ml/min, and the following fractions were collected:

| Fraction No. | Color | Volume (ml) |
| --- | --- | --- |
| 8 | pale straw | 123.3 |
| 9 | none | 45.0 |

Fraction No. 8 was reduced to a thick, pale-yellow syrup by vacuum evaporation at 98° C. To this was added 25 ml of water and the evaporation was repeated to remove the last of the ammonia. On standing for 48 hours at room temperature, the oily residue yielded large, fern leaf-shaped crystals of L-β-3, confirmed by TLC in parallel with pure, authentic substance. Fraction Nos. 8 and 9 together yielded a total of 46.9 mg of L-β-3. Fraction Nos. 4, 5, and 6 together yielded a total of 192 mg of substance which was mostly L-phenylalanine with a lesser amount of L-tyrosine and a trace amount of L-β-3, as shown by TLC analysis.

EXAMPLE 3

Adsorptive Separation Of L-Phenylalanine, L-Tyrosine, And L-β-3 From Non-Aromatic Amino Acids In A Batch Process 240 grams of AMBERLITE® XAD-4 resin was successively pre-washed with 2.0 liters of water, 1.1 liter of 91% isopropyl alcohol, and 5.5 liters of water and then placed in a 1.5 liter beaker equipped with a mechanical stirrer.

78.00 grams of the amino acid mixture was dissolved in 780 ml of water and added to the beaker containing the resin. The mixture was stirred for 1.0 hour at room temperature (22° C.), at a rate sufficient to maintain the resin in a uniform suspension.

The resin was filtered off in a Buchner funnel equipped with a coarse grade of filter paper (Whatman #1). The yellow filtrate was identified as Filtrate No. 1 and stored under refrigeration for later use.

The resin was returned to the beaker, stirred with 250 ml of water for 15 minutes (a slightly longer time does not affect the process), and filtered. The pale yellow filtrate was identified as Filtrate No. 2 and refrigerated for later use.

The water wash was repeated and the Filtrate No. 3 was refrigerated.

The resin was returned to the beaker and stirred with 250 ml of 2% aqueous acetic acid for 15 minutes at room temperature. The resin was filtered off and the colorless filtrate was identified as Filtrate No. 4 and preserved under refrigeration for later use.

The resin was returned to the beaker and washed twice, 10 minutes per wash, with 240 ml portions of water, and filtered after each wash. These water washes were identified as Filtrate Nos. 5 and 6, and held under refrigeration for later use.

The resin was returned to the beaker and stirred for 15 minutes with 250 ml of 1 N ammonium hydroxide. The resin was separated by filtration and the pale straw-colored filtrate was identified as Filtrate No. 7.

The resin was returned to the beaker and washed twice, 10 minutes per wash, with 240 ml portions of water, filtering after each wash. The filtrates were identified as Filtrate Nos. 8 and 9, and held under refrigeration for later use.

As Filtrate No. 7 was expected to contain the major portion of the recoverable L-β-3, it was immediately vacuum-evaporated at 98° C., the residue twice re-dissolved in 25 ml portions of water and re-evaporated under vacuum to remove all of the ammonia. The fully dried off-white residue weighed 355 mg (445 expected) and was shown by TLC in parallel with a standard to be substantially pure L-β-3 with no more than a trace of L-phenylalanine and no L-tyrosine. When this sample was dissolved/suspended in 5.0 ml of water and refrigerated, it was converted to a crystalline mass over a period of several days. Filtration and drying provided 271.3 mg of substantially pure, crystalline product, L-β-3.

An aliquot of Filtrate No. 1 was vacuum-evaporated to dryness at 98° C. The weight recovered corresponded to a weight of 59.0 g in Filtrate No. 1. TLC revealed the presence of mixed aliphatic amino acids, no L-phenylalanine, no L-β-3, and a faint trace of L-tyrosine. Therefore the entire Filtrate No. 1 was spray-dried under vacuum and mild heat to produce a pale tan powder weighing (in total) 58.5 g and possessing a pleasant, slightly meaty flavor with a sweet background note.

Investigation of Filtrate No. 4 revealed that it contained 2.55 g of solids (dry) which, based upon TLC analysis, consisted of a mixture of L-phenylalanine and a relatively minor amount of L-tyrosine. No other amino acids were apparent in this product.

Finally, Filtrate No. 8 was investigated and found to contain 32 mg of L-β-3 (TLC).

EXAMPLE 4

13% L-β-3 Admixed With Aliphatic Amino Acids By Dry Compounding

A mixture of 13.0 g of L-β-3 and 87.0 g of spray-dried aliphatic amino acids (consisting of glycine and the L-forms of alanine, arginine, aspartic acid, cysteine, glutamic acid, histidine, isoleucine, leucine, lysine, methionine, proline, serine, threonine, and valine, obtained, for example, from Filtrate No. 1 of Example 3) was placed in a small ball-mill equipped with ceramic balls, and milled for 4.0 hours at ambient temperature. The resulting fine, light-tan powder was found to have a total nitrogen content of 13.1% and a pleasant, slightly meat-like odor and flavor.

EXAMPLE 5

25% L-β-3 Admixed With Aliphatic Amino Acids By Aqueous Compounding

As was noted in Example 3, Filtrate No. 7 was found to contain 355 mg of L-β-3 in 250 ml of solution and Filtrate No. 1 contained 58.5 g of mixed aliphatic amino acids in a volume of 780 ml. Therefore, in a fractionation experiment identical to that of Example 3, the entire Filtrate No. 7, 240 ml, was combined with 14.2 ml of Filtrate No. 1 (which was calculated to contain 1065 mg of mixed aliphatic amino acids) and the entire solution evaporated to dryness under vacuum at 98° C. It was re-evaporated to dryness each time after 2 successive additions of 40 ml of water, until the condensate from the evaporation was neutral, showing that all of the ammonia had been displaced. The remaining dry solid, 1.32 g, was found on three successive analyses of samples taken randomly from the mixture to have total nitrogen content of 13.2%, 13.3%, and 13.3%. The total nitrogen content is noticeably greater than that of the starting material, probably because of the formation of ammonium salts of aspartic and glutamic acids in the mixed aliphatic amino acids during exposure to the excess ammonium hydroxide present in Filtrate No. 7.

As will be apparent to one skilled in the art, various modifications can be made within the scope of the aforesaid description. Such modifications, being within the ability of one skilled in the art, form a part of the present invention and are embraced by the appended claims.

1. *Harper's Biochemistry*, 21st Ed. 1988. R. K. Murray, D. K. Granner, P. A. Mayes and V. W. Rodwell. Section V. Biochemistry of Extracellular & Intracellular Communication, pp 445–462. Appleton & Lange. Norwalk, Connecticut/San Mateo, Calif.
2. "Evaluation of L-tryptophan for Treatment of Insomnia: A Review". D. Schneider-Helmert and C. L. Spinweber, *Psychopharmacology* (1986) 89:1–7.
3. "L-tryptophan: A Rational Hypnotic with Clinical Potential". E. Hartmann. *Am. J. Psychiatry* (1977) 134(4): 366–370.
4. "Dietary Effects on Brain Serotonin Synthesis: Relationship to Appetite Regulation". J. D. Fernstrom. *Am. J. Clin. Nutr.* (Nov. 1985)42:1072–1082.
5. "Acute Tryptophan Depletion and Increased Food Intake and Irritability in Bulimia Nervosa". T. E. Weltzin, M. H. Fernstrom, J. D. Fernstrom, S. K. Neuberger and W. H. Kaye, *Am. J. of Psychiatry* (1995) 152(11):1668–1671.
6. "The Effect of Low Brain Serotonin on Mood and Aggression in Humans. Influence of Baseline Mood and Genetic Factors." S. N. Young, R. O. Pihl, C. Benkelfat, R. Palmour, M. Ellenbogen and D. Lemarquand. *Recent Advances in Tryptophan Research*. Ed. G. A. Filippini et al, pp. 45–50, Plenum Press, New York, 1996.
7. "Tryptophan Depletion and Aggressive Responding in Healthy Males". F. G. Moeller, D. M. Dougherty, A. C. Swann, D. Collins, C. M. Davis and D. R. Cherek. *Psychopharmacology*, (1996) 126:97–103.
8. "Aggression and Personality: Association with Amino Acids and Monoamine Metabolites". S. E. Moller, E. L. Mortensen, L. Breum, C. Alling, O. G. Larsen, T. Boge-Rasmussen, C. Jensen and K. Bennicke. *Psychological Medicine* (1996) 26:323–331.
9. "The Effects of Dietary Tryptophan on Chronic Maxillofacial Pain and Experimental Pain Tolerance". S. Seltzer, D. Dewart, R. L. Pollack and E. Jackson. *J. Psychiat. Res.* (1982/1983) 17 (2):181–186.
10. "Alteration of Human Pain Thresholds by Nutritional Manipulation and L-Tryptophan Supplementation". S. Seltzer, R. Stoch, R. Marcus and E. Jackson. *Pain* (1982) 13:385–393.
11. "Effects of Altering Brain Serotonin Activity on Human Chronic Pain". In *Advances in Pain Research and Therapy*. J. J. Bonica and Albe-Fissard, Eds. Vol. 1, 601–606. Raven Press 1976, New York.

It is claimed:

1. A process for isolating substantially pure L-β-3-indolylalanine (L-β-3) from a source of amino acids including L-β-3, L-phenylalanine, L-tyrosine and aliphatic amino acids; said process comprising passing an aqueous solution of the source of amino acids over a porous wettable nonionic polymeric resin, said resin being attractive to aromatic amino acids and having substantially no attraction to aliphatic amino acids, to allow a substantial portion of L-β-3, L-phenylalanine and L-tyrosine to adsorb to said resin and to provide a first solution containing aliphatic amino acids;

elution of said resin with deionized water to displace any residual aliphatic amino acids from the resin to provide a second solution containing aliphatic amino acids;

elution of said resin with a dilute solution of an acid to displace L-phenylalanine and L-tyrosine from the resin and provide a third solution containing L-phenylalanine and L-tyrosine, said acid being a short chain aliphatic acid having a molecular weight no greater than 88.10 daltons and a $K_a$ between from $1.77 \times 10^{-4}$ to $1.34 \times 10^{-5}$ at 25° C.;

elution of the resin with a base in dilute form to displace L-β-3 from the resin and provide a fourth solution containing L-β-3 displaced from said resin, said base being selected from a group consisting of ammonia, and short chain aliphatic primary, secondary and tertiary amines having a molecular weight no greater than 101.19 daltons and a $K_b$ between from $1.26 \times 10^{-3}$ to $1.8 \times 10^{-5}$ at 25° C.; and recovering L-β-3 from the fourth solution.

2. A batch process for isolating substantially pure L-β-3-indolylalanine (L-β-3) from a source of amino acids including L-β-3, L-phenylalanine, L-tyrosine and aliphatic amino acids; said batch process comprising exposing through contact an aqueous solution of the source of amino acids to a porous wettable nonionic polymeric resin, said resin being attractive to aromatic amino acids and having substantially no attraction to aliphatic amino acids, for a time sufficient to adsorb to said resin a substantial portion of L-β-3, L-phenylalanine and L-tyrosine present in said aqueous solution of the source of amino acids and to provide a supernatant containing aliphatic amino acids;

separating said polymeric resin from said supernatant;

washing said polymeric resin with water to remove any residual aliphatic amino acids;

eluting the polymeric resin with a dilute solution of an acid to displace from said polymeric resin L-phenylalanine and L-tyrosine and provide a solution of L-phenylalanine and L-tyrosine, said acid being a short chain aliphatic acid having a molecular weight no greater than 88.10 daltons and a $K_a$ between from $1.77 \times 10^{-4}$ to $1.34 \times 10^{-5}$ at 25° C.;

washing the polymeric resin with water to remove the acid therefrom;

eluting the polymeric resin with a base in dilute form to displace L-β-3 therefrom and provide a solution of L-β-3 displaced from the polymeric resin, said base being selected from a group consisting of ammonia, and short chain aliphatic primary, secondary and tertiary amines having a molecular weight no greater than 101.19 daltons and a $K_b$ between from $1.26 \times 10^{-3}$ to $1.8 \times 10^{-5}$ at 25° C.; and recovering L-β-3 from the solution containing L-β-3 displaced from the polymeric resin.

3. A process according to claim 1 or 2 wherein the source of amino acids is a protein hydrolysate of natural proteins.

4. A process according to claim 3 wherein the protein hydrolysate is an enzymatic hydrolysate of casein.

5. A process according to claim 3 wherein the protein hydrolysate is an enzymatic hydrolysate of soy protein.

6. A process according to claim 1 or 2 wherein said acid is selected from a group consisting of acetic acid, formic acid, propionic acid, butyric acid and i-butyric acid.

7. A process according to claim 1 or 2 wherein said base is selected from a group consisting of ammonia, trimethylamine, triethylamine, $(CH_3)_2NH$, $(C_2H_5)_2NH$, $CH_3NH_2$ and $CH_2CH_2NH_2$.

8. A process according to claim 1 or 2 wherein recovery of the L-β-3 is by evaporation.

9. A process according to claim 1 or 2 wherein recovery of the L-β-3 is by crystallization.

10. A process according to claim 1 or 2 wherein the resin is a nonionic cross-linked polystyrene.

11. A process according to claim 1 or 2 wherein the polymeric resin is in particulate form.

12. A process according to claim 11 wherein said particulate form is bead form.

13. A process according to claim 2 wherein said separating of the polymeric resin from said supernatant is by filtration.

14. A process according to claim 2 wherein said separating of the polymeric resin from said supernatant is by centrifugation.

* * * * *